United States Patent
Ishii et al.

(10) Patent No.: US 8,545,404 B2
(45) Date of Patent: Oct. 1, 2013

(54) EYEBALL TISSUE CHARACTERISTIC FREQUENCY MEASUREMENT DEVICE AND NON-CONTACT TONOMETER UTILIZING THE SAME

(75) Inventors: Kotaro Ishii, Tsukuba (JP); Toshihiro Kameda, Tsukuba (JP)

(73) Assignee: University of Tsukuba, Tsukuba-shi (JP)

( * ) Notice: Subject to any disclaimer, the term of this patent is extended or adjusted under 35 U.S.C. 154(b) by 360 days.

(21) Appl. No.: 12/992,646

(22) PCT Filed: May 14, 2009

(86) PCT No.: PCT/JP2009/058977
§ 371 (c)(1),
(2), (4) Date: Feb. 7, 2011

(87) PCT Pub. No.: WO2009/139435
PCT Pub. Date: Nov. 19, 2009

(65) Prior Publication Data
US 2011/0118585 A1     May 19, 2011

(30) Foreign Application Priority Data
May 15, 2008 (JP) .................................. 2008-128690

(51) Int. Cl.
*A61B 5/00* (2006.01)
(52) U.S. Cl.
USPC ........................................................ 600/401
(58) Field of Classification Search
USPC ................................................. 600/398–401
See application file for complete search history.

(56) References Cited

U.S. PATENT DOCUMENTS

| | | | |
|---|---|---|---|
| 5,251,627 | A | 10/1993 | Morris |
| 5,372,030 | A | 12/1994 | Prussia et al. |

(Continued)

FOREIGN PATENT DOCUMENTS

| | | |
|---|---|---|
| JP | 09-103411 A | 4/1997 |
| JP | 2004-267299 A | 9/2004 |

(Continued)

OTHER PUBLICATIONS

Francesco Viola et al.,"Radiation Force Imaging of Viscoelastic Properties with Reduced Artifacts"; IEEE Transaction on Ultrasonics, Ferroelectrics, and Frequency Control; vol. 50, No. 6, pp. 736-742 (2003).

(Continued)

*Primary Examiner* — Max Hindenburg
(74) *Attorney, Agent, or Firm* — Marvin A. Motsenbocker; Mots Law, PLLC (57) ABSTRACT

A non-contact tonometer of the present invention quantitatively measures characteristic vibration of the cornea of an eyeball and measures a true ocular pressure utilizing this vibration, and comprises: an air flow spray unit (200) spraying an air flow (F) to a cornea (C) of an eye (E) to be examined and deforming the cornea; a cornea deformation amount measurement unit (300) measuring deformation of the cornea caused by the air flow spray unit along with elapsed time from the start of the air flow spray; a Fourier analysis unit (401) performing Fourier analysis on a relationship between a deformation amount of the cornea obtained by a cornea deformation detection unit and the elapsed time; an eyeball tissue characteristic frequency operation unit (402) obtaining an characteristic frequency of each constituent tissue of the eyeball based on a Fourier analysis result obtained by the Fourier analysis unit; and an ocular pressure operation unit (403) calculating an ocular pressure based on the characteristic frequency of the cornea obtained by the eyeball tissue characteristic frequency operation unit.

5 Claims, 8 Drawing Sheets

(56) References Cited

U.S. PATENT DOCUMENTS

| | | | |
|---|---|---|---|
| 5,903,334 A * | 5/1999 | Sakurai et al. | 351/200 |
| 6,595,920 B2 * | 7/2003 | Walton | 600/401 |
| 7,708,406 B2 * | 5/2010 | Koest | 351/208 |
| 7,798,962 B2 * | 9/2010 | Luce | 600/405 |
| 7,871,378 B1 * | 1/2011 | Chou et al. | 600/398 |
| 2003/0187342 A1 | 10/2003 | Cuzzani et al. | |
| 2004/0046937 A1 | 3/2004 | Zemmouri et al. | |
| 2004/0079155 A1 | 4/2004 | Omata | |
| 2007/0055122 A1 | 3/2007 | Luce | |

FOREIGN PATENT DOCUMENTS

| | | |
|---|---|---|
| JP | 2005-521449 A | 7/2005 |
| JP | 2005-521450 A | 7/2005 |
| JP | 2006-262990 A | 10/2006 |
| JP | 2007-69008 A | 3/2007 |
| JP | 2007-202734 A | 8/2007 |
| WO | 03/082086 A | 10/2003 |
| WO | 03/082087 A | 10/2003 |

OTHER PUBLICATIONS

Kotaro Ishii et al.;"A numerical analysis of non-contact tonometer using finite element method"; Journal of Japanese Ophthalmological Society; Special Extra Issue; vol. 112, p. 318 and cover pages (2008) ; and its partial English translation.

Tetsuro Oshika et al.;"Physiological anatomy for ophthalmological clinic"; Ophthalmology practice 6; pp. 152-157 and cover page (2005); and its partial English translation.

Zhigang Sun et al."Investigation of Postoperative Refractive Change after Scleral Buckling Surgery Using FEM Numerical Simulation"; Journal of Japan Society for Computer Aided Surgery, vol. 13, No. 2, 3, pp. 53-60, 200 (2005).

* cited by examiner

EYEBALL TISSUE CHARACTERISTIC FREQUENCY MEASUREMENT DEVICE AND NON-CONTACT TONOMETER UTILIZING THE SAME

TECHNICAL FIELD

The present invention relates to an eyeball tissue characteristic frequency measurement device for an eye to be examined and a non-contact tonometer for measuring an ocular pressure in a non-contact manner utilizing the same.

BACKGROUND TECHNOLOGY

Glaucoma ranks high among the causes of blindness, and, although the prevalence is 3 to 5% for people 40 years old or more, many patients are not conscious of the disease in the current situation since the symptom of the impaired eyesight does not appear until the last stage.

An ocular pressure test by a non-contact tonometer is one of test methods used most widely for a screening test of the glaucoma, and is important for early detection of the illness. Further, ocular pressure reduction is only the treatment which has a scientific basis in a glaucoma treatment and the ocular pressure measurement is extremely important for determining the effect of the treatment.

Currently, almost all the commercially available tonometers except a Schiotz tonometer employ a measurement method using that of a Goldmann applanation tonometer (GAT) as a standard, and calculate an intraocular pressure as "ocular pressure" by converting an external force required to applanate a part of a cornea (Non-patent document 1). Accordingly, a measurement device measuring the hardness of a cornea surface is currently distributed as the tonometer on the market.

However, actually, the true intraocular pressure and the stiffness of the cornea itself cannot be measured separately from the hardness of the cornea surface, and it has been pointed out that a conventional tonometer has a measurement error caused by an individual structural difference such as a thickness or a curvature of the cornea and an individual material difference of the cornea.

Recently, there has been proposed a measurement method to clarify the physical property of an eyeball such as the stiffness of a cornea by using a device, so called a non-contact tonometer, which measures an intraocular pressure from eyeball deformation when an air flow is sprayed to an eyeball (Patent document 1 and Patent document 2). This measurement method is also based on the measurement of the hardness of an eyeball surface and the measurement principle thereof is a regression method obtained experimentally from a clinical database, and therefore a physical amount is not clarified as an absolute value. Accordingly, this method does not have a basis of measuring a true ocular pressure. Further, another non-contact ocular pressure measurement attempts to measure the intraocular pressure from a vibration such as an acoustic wave and resonance of the eyeball (Patent document 3). Such a method from resonance phenomenon cannot discriminate each eyeball tissue such as a cornea and a sclera, and has a problem that accuracy is not sufficient because the method is considerably affected by a tissue attached to the eyeball such as an external eye muscle, an optical nerve, and an orbital fat.

While some measurement methods utilizing the resonance have been applied to a contact tonometer, the situation about the cause of a measurement error is similar to that in the non-contact type (Patent documents 4 to 6).

Meanwhile, another report about the eyeball physical property shows a numerical simulation of eyeball deformation using a finite element method (Non-patent document 2). This study shows that actual eyeball deformation can be reproduced by the numerical simulation of the eyeball deformation using the finite element method.

RELATED ART DOCUMENTS

[Patent Documents]
Patent document 1: Japanese Patent Application Laid-Open Publication No. 2006-262990
Patent document 2: Japanese Patent Application Laid-Open Publication No. 2007-69008
Patent document 3: Japanese Patent Application Laid-Open Publication No. 2005-521450
Patent document 4: Japanese Patent Application Laid-Open Publication No. 2004-267299
Patent document 5: Japanese Patent Application Laid-Open Publication No. 2005-521449
Patent document 6: Japanese Patent Application Laid-Open Publication No. 2007-202734

[Non-Patent Documents]
Non-patent document 1: "Ophthalmic practice 6: anatomical physiology necessary for ophthalmic clinic" pp. 152-157, Bunkodo
Non-patent document 2: Zhi-gang et al. "Investigation of Postoperative Refractive Change after Scleral Buckling Surgery Using FEM Numerical Simulation" Journal of Japan Society for Computer Aided Surgery, Vol. 13, No. 2, 3, pp. 53-60, 2005

OUTLINE OF INVENTION

Problems to be Solved by Invention

The present invention has been achieved in view of the problem of the above conventional art, and aims at providing an eyeball tissue characteristic frequency measurement device which can quantitatively measure characteristic vibration of a cornea and other tissues such as a sclera and a Zinn's zonule, which are tissues constituting an eyeball, and contribute to the development of the physical property analysis of the eyeball.

Further, the present invention aims at providing a non-contact tonometer capable of measuring a true ocular pressure which has been unable to be measured so far.

Means to Solve the Problems

An eyeball tissue characteristic frequency measurement device of the present invention comprises: an air flow spray unit spraying an air flow to a cornea of an eye to be examined and deforming the cornea; a cornea deformation amount measurement unit measuring deformation of the cornea caused by the air flow from the air flow spray unit along with elapsed time from the start of the air flow spray; a Fourier analysis unit performing Fourier analysis on a relationship between a deformation amount of the cornea obtained by the cornea deformation amount measurement unit and the elapsed time; and an eyeball tissue characteristic frequency operation unit obtaining a characteristic frequency of each constituent tissue of an eyeball based on a Fourier analysis result obtained by the Fourier analysis unit.

In the eyeball tissue characteristic frequency measurement device of the above invention, the cornea deformation amount measurement unit may be a high-speed camera.

Further, in the eyeball tissue characteristic frequency measurement device of the above invention, the cornea deformation amount measurement unit may be a laser displacement sensor.

Further, in the eyeball tissue characteristic frequency measurement device of the above invention, the Fourier analysis unit may include a numerical simulation result preserving unit preserving a numerical simulation result of eyeball deformation and a pattern classification unit performing pattern classification for determining to which tissue characteristic frequency of the eyeball a Fourier-analyzed time function corresponds.

Further, in the eyeball tissue characteristic frequency measurement device of the above invention, the eyeball tissue characteristic frequency operation unit may obtain a characteristic frequency of a cornea, a sclera, or a Zinn's zonule of the eyeball.

Further, the present invention provides a non-contact tonometer utilizing an eyeball tissue characteristic frequency measurement device which comprises an ocular pressure operation unit calculating an ocular pressure based on the characteristic frequency of the cornea of the eyeball obtained by the eyeball tissue characteristic frequency operation unit.

Effect of the Invention

The present invention can provide the notification of a true ocular pressure which has been unable to be measured so far. While the conventional measurement method is based on the measurement of the hardness of the cornea surface, the present invention measures a stress caused in the cornea by a true intraocular pressure using the characteristic vibration of the cornea and has a different basic principle from the conventional ocular pressure measurement. Further, the quantitative measurement for the characteristic vibration of the cornea and the other eyeball tissues, which cannot be discriminated from one another by the resonance phenomenon or the like, has not been reported so far and this measurement method can contribute to the development of the eyeball physical property analysis.

That is, the eyeball tissue characteristic frequency measurement device of the present invention deforms the cornea by spraying an air flow to the cornea of an eye to be examined, measures this cornea deformation amount along with elapsed time from the start of the air flow spray, performs the Fourier analysis on the relation between the cornea deformation amount and the elapsed time, and obtains the characteristic frequency of each tissue constituting an eyeball based on the obtained Fourier analysis result, and thereby can quantitatively measure the characteristic vibration of the cornea and the other eyeball tissues.

Further, the present invention calculates the ocular pressure based on the characteristic frequency of the cornea obtained by the eyeball tissue characteristic frequency measurement device, and thus can measure the stress caused in the cornea by the true intraocular pressure using the characteristic vibration of the cornea.

EMBODIMENTS

Hereinafter, an embodiment of the present invention will be explained in detail in accordance with the drawings.

(First Embodiment)

Figure 1:
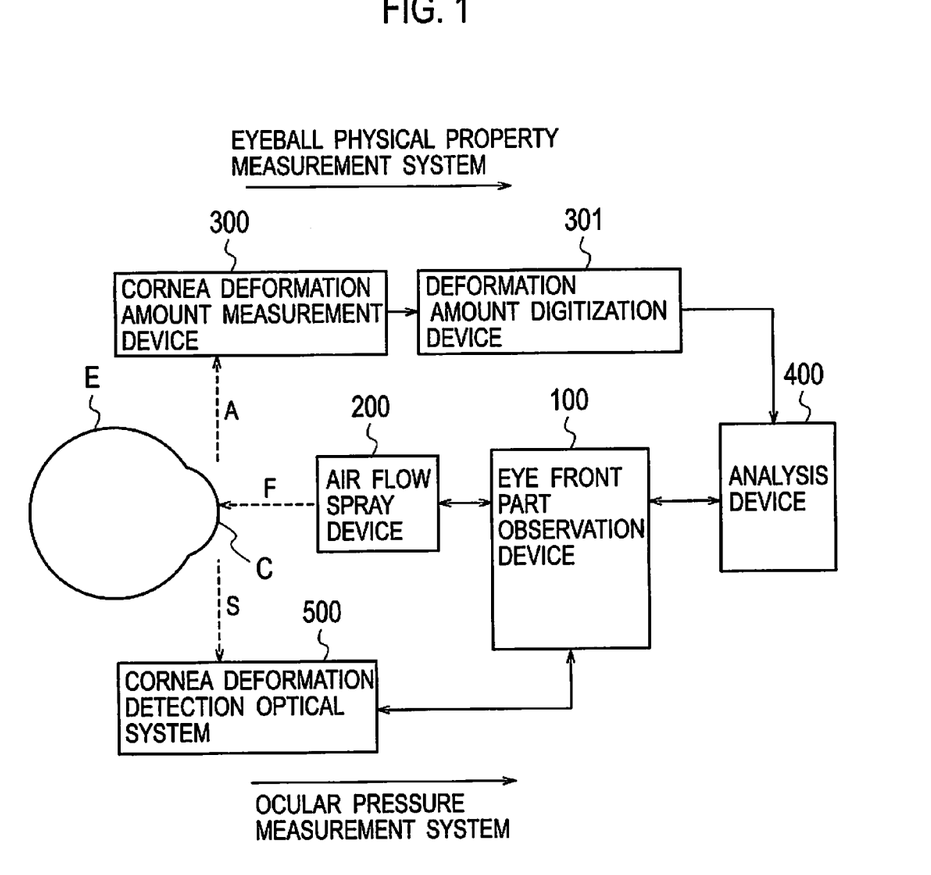
FIG. 1 is a block diagram of a non-contact tonometer in a first embodiment of the present invention.

FIG. 1 shows an entire device configuration of a non-contact tonometer in an embodiment of the present invention. The non-contact tonometer of the present embodiment is provided with: an eye front part observation device 100; an air flow spray device 200 which sprays an air flow to the top of a cornea and deforms the cornea; a deformation amount measurement device 300 which continuously photographs a cornea C of an eye E to be examined from a side with a high-speed camera having a high sensitivity and measures a deformation amount of the cornea C at each photographing time; a deformation amount digitization device 301 which digitizes the deformation amount of the cornea C in correspondence with an elapsed time after the timing of the air flow spray; and an analysis device 400 which calculates an ocular pressure value, an eigenfrequency of each tissue constituting an eyeball, and the like using data obtained by the series of detection systems. Further, the non-contact tonometer of the present embodiment is provided with a cornea deformation detection optical system 500 which optically observes the cornea deformation within the eye front part observation device 100.

Figure 2:
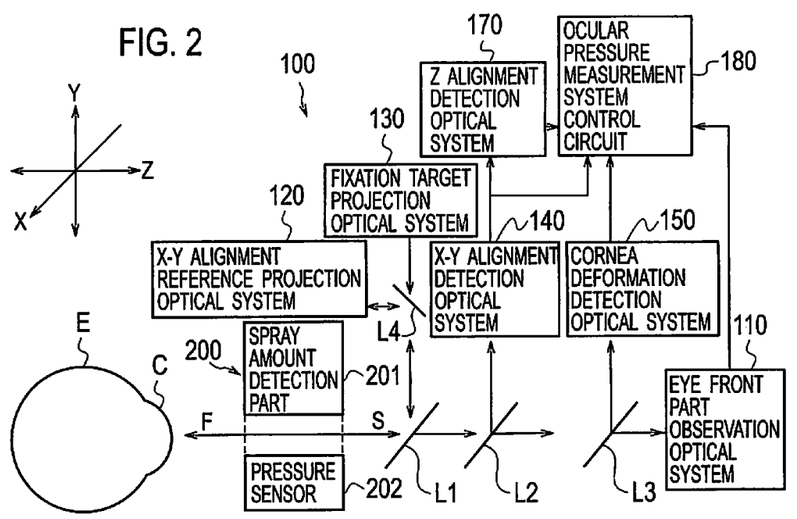
FIG. 2 is a plan view of an optical system arrangement in the non-contact tonometer of the embodiment.
Figure 3:
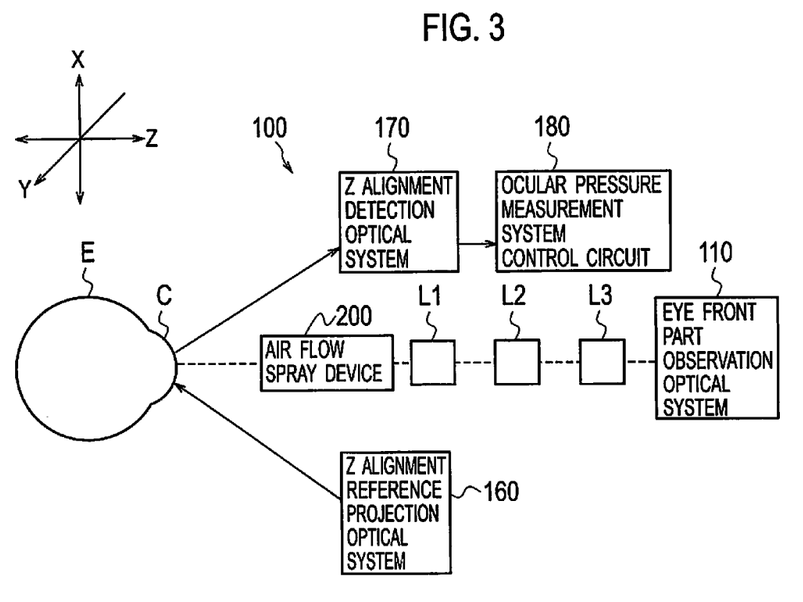
FIG. 3 is a side view of an optical system arrangement in the non-contact tonometer of the embodiment.

As shown in FIG. 2 and FIG. 3, the eye front part observation device 100 is provided with: an eye front part observation optical system 110 which observes an eye front part of the eye E to be examined; an X-Y alignment reference projection optical system 120 which projects an reference light for detecting alignment in the X-Y direction and detecting the cornea deformation onto the cornea C of the eye E to be examined from the front; a fixation target projection optical system 130 which provides a fixation target to the eye E to be examined; an X-Y alignment detection optical system 140 which detects a positional relationship between the eye front part observation device 100 and the X-Y direction of the cornea C by receiving reflected light of the X-Y alignment reference light from the cornea C; a cornea deformation detection optical system 150 which detects the deformation amount of the cornea C by receiving the reflected light of the X-Y alignment reference light from the cornea C; a Z alignment reference projection optical system 160 which projects reference light for Z direction alignment obliquely onto the cornea C; a Z alignment detection optical system 170 which receives reflected light of the Z alignment reference light from the cornea C in a direction symmetrical to the optical axis of the eye front part observation optical system 110 and detects a positional relationship between the eye front part observation device 100 and the Z direction of the cornea C; and an ocular pressure measurement system control circuit 180. Here, in FIG. 2 and FIG. 3, each of L1 to L4 indicates a half mirror, F indicates an air flow, and S indicates laser light.

An air flow spray device 200 is provided with a spray amount detection part 201 which detects an amount of air sprayed to the eye E to be examined and a pressure sensor 202 which measures an inner pressure within the device at a certain time when the air flow is sprayed.

In the non-contact tonometer of the present embodiment, the air flow spray device 200 sprays the air flow to the top of cornea C of the eye E to be examined and deforms the cornea C. Then, the deformation amount measurement device 300 continuously photographs the cornea C of the eye E to be examined from a side with a high-speed camera having a high sensitivity, and measures a temporal transition of the deformation of the cornea C. Then, the deformation amount digitization device 301 digitizes and records the temporal transition of the deformation amount of the cornea C after the timing of the air flow spray. The analysis device 400 calculates the ocular pressure, the characteristic frequency of each tissue constituting the eyeball, and the like using the data obtained from the series of detection system in operation processing to be described hereinafter. Together with the above, in the non-contact tonometer of the present embodiment, the cornea deformation detection optical system 500 optically observes the cornea deformation within the eye front part observation device 100.

In the eye front part observation device 100, the eye front part optical system 110 observes the eye front part of the eye E to be examined. The X-Y alignment reference projection optical system 120 projects the laser reference light for detecting the alignment in the X-Y direction and detecting the cornea deformation onto the cornea C of the eye E to be examined from the front and the fixation target projection optical system 130 projects the fixation target onto the eye E to be examined at the same time. Then, the X-Y alignment detection optical system 140 receives reflected laser light S of the X-Y alignment reference light from the cornea C and detects the positional relationship between the eye front part observation device 100 and the X-Y direction of the cornea C, and the cornea deformation detection optical system 150 receives the reflected light S of the X-Y alignment reference light from the cornea C and detects the deformation amount of the cornea C.

Further, the Z alignment reference projection optical system 160 projects the reference light for the Z direction alignment obliquely onto the cornea C, and the Z alignment detection optical system 170 receives reflected light of the Z alignment reference light from the cornea C in a direction symmetric to the optical axis S of the eye front part observation optical system 110 and detects the positional relationship between the eye front part observation device 100 and the Z direction of the cornea C.

The series of non-contact ocular pressure measurement methods performed in this eye front part observation device 100 and the air flow spray device 200, which sprays the air flow to the top of the cornea and deforms the cornea, to the ocular pressure measurement system control circuit 180 are the same as the conventional method as described in Japanese Patent Application Laid-Open Publication No. 2000-212, for example. Simple explanation thereof is as follows.

The X-Y alignment reference projection optical system 120 emits laser projection light, causes the laser projection light to pass through the inside of the air flow spray device 200 after having been reflected by the half mirrors L4 and L1, to irradiate the top part of the cornea C of the eye E to be examined as the X-Y alignment reference light, and obtains the reflected laser light S.

Meanwhile, the fixation target projection optical system 130 emits the fixation target light, causes the fixation target light to pass through the inside of the air flow spray device 200 after having been reflected by the half mirror L1, and guides the fixation target light to the eye E to be examined. A subject watches the fixation target as a fixed visual target and the line of sight of the subject is fixed.

The X-Y alignment detection optical system 140 takes in the reflected light S, which is projected onto the cornea C by the X-Y alignment reference projection optical system 120 and reflected by the cornea surface, by causing the reflected light S to be reflected by the half mirror L2, calculates the positional relationship (X-Y direction) between the eye front part observation device 100 and the cornea C using this reflected light S, and outputs the operation result to the Z alignment detection optical system 170 and the ocular pressure measurement system control circuit 180.

Further, a part of the reflected light S which has been reflected by the cornea surface is reflected by the half mirror L3 and guided to the cornea deformation detection optical system 150.

On the other hand, the laser projection light emitted from the Z alignment reference projection optical system 160 is guided to the cornea C of the eye E to be examined, reflected by the cornea surface, and guided to the Z alignment detection optical system 170.

The subject of the ocular pressure measurement, while observing the eye front part image on a monitor screen of the eye front part observation optical system 110, manually moves this device 100 in the X-Y-Z direction and performs alignment adjustment such that the projection light meets a target position and also is focused there. Then, the air flow spray device 200 is operated, the air flow F is sprayed to the cornea C, and the cornea deformation amount at this time is detected by the cornea deformation detection optical system 150.

Figure 4:
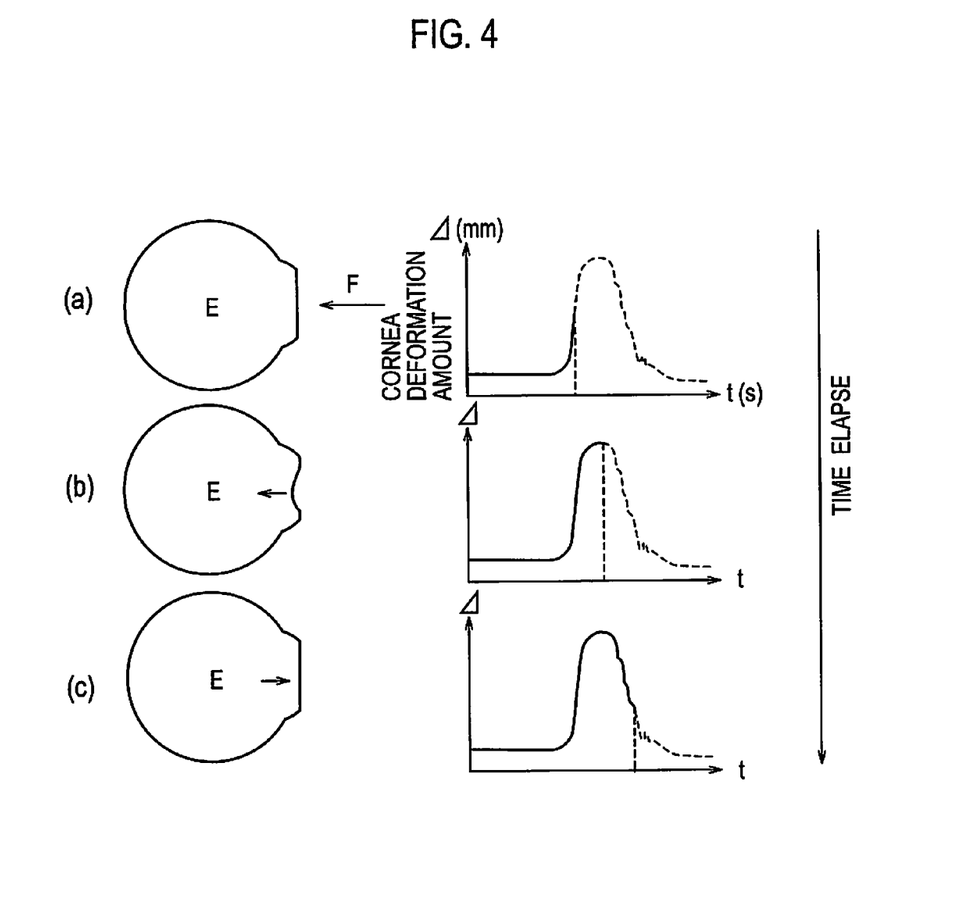
FIG. 4 is an explanatory diagram explaining a process of converting a temporal cornea deformation into a graph in a non-contact tonometer of the embodiment.

FIG. 4 shows a state of deformation behavior in the cornea C observed temporally by the cornea deformation amount measurement device 300 when the air flow is sprayed to the cornea C of the eye E to be examined, and shows a temporal transition graph of the deformation amount of the cornea C which is digitized by the deformation amount digitization device 301, in the non-contact tonometer of the present embodiment. The temporal transition of the cornea deformation amount obtained by these devices is shown in FIG. 5 as a time function g(t).

Figure 6:
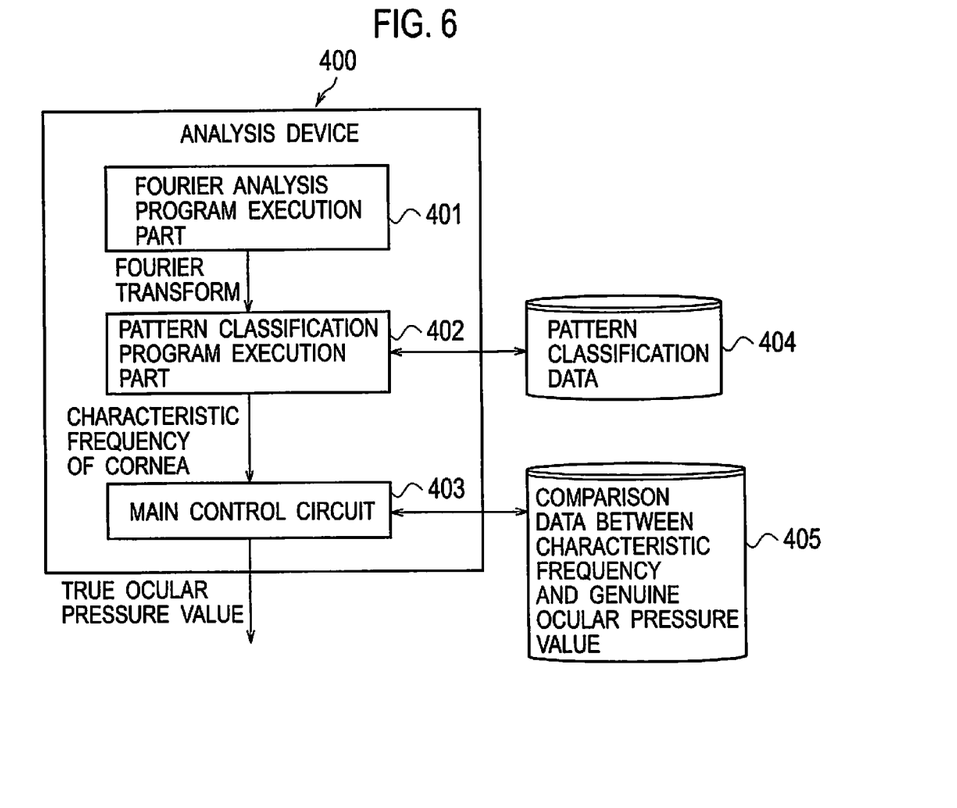
FIG. 6 is a block diagram of an internal configuration of an analysis device in a non-contact tonometer of the embodiment.

As shown in FIG. 6, the analysis device 400 is provided with a Fourier analysis program 401 which analyzes a time function of the digitized cornea deformation amount $\Delta$ by the Fourier analysis. The analysis device 400 is further provided with a pattern classification program 402 which performs pattern classification determining to which physical component of an eyeball a Fourier-transformed component of a time function corresponds which is obtained from a numerical simulation of eyeball deformation using a finite element analysis of the eyeball. The analysis device 400 is also provided with a main control circuit 403 which digitizes and outputs a physical property using a coefficient of a graph obtained by the classification. The main control circuit 403 also digitizes and outputs an ocular pressure value using data obtained by the ocular pressure measurement system control circuit 180 in the eye front part observation device 100.

Figure 5:
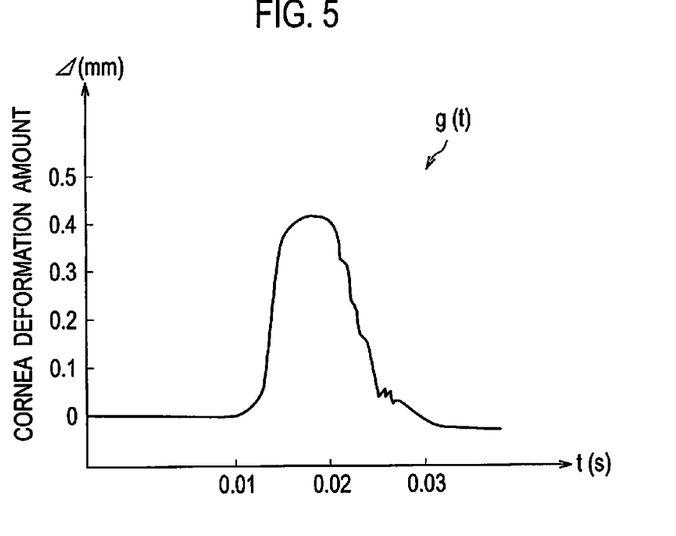
FIG. 5 is a graph showing a time function of a cornea deformation amount digitized by a non-contact tonometer of the embodiment.

The function g(t) shown by the graph of FIG. 5 is a function of time t of a non-cyclic function and is Fourier-transformed by the Fourier analysis program 401 to be expressed as a Fourier transform expression formula as shown by the following Formula (1).

[Formula 1]

$$g(t) = \frac{1}{2\pi} \int_{-\infty}^{\infty} G(\omega) e^{i\omega t} d\omega \qquad (1)$$

Then, the Fourier transform G(ω) of the function g(t) is expressed as a function of an angular frequency ω as shown by Formula (2).

[Formula 2]

$$G(\omega) = \int_{-\infty}^{\infty} g(t) e^{-i\omega t} dt \qquad (2)$$

Figure 7:
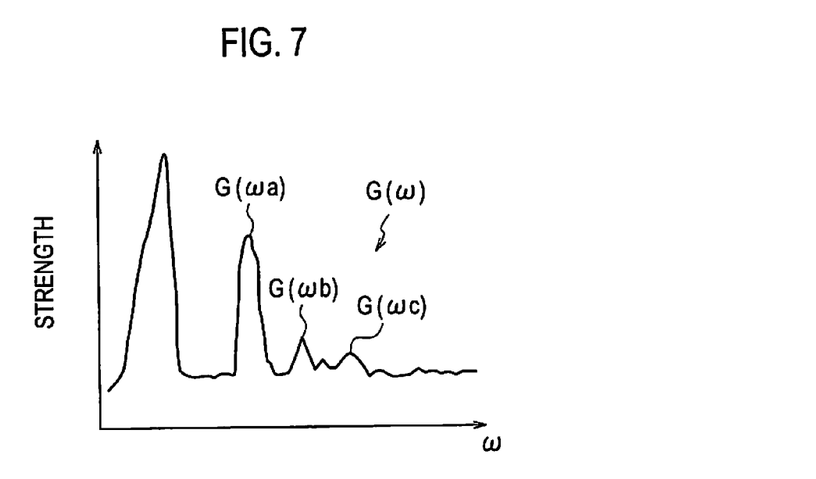
FIG. 7 is a Fourier transform chart of the graph in FIG. 5 provided by a non-contact tonometer of the embodiment.

FIG. 7 shows a graph of G(ω) obtained by Fourier-transforming the graph of FIG. 5.

Figure 8:
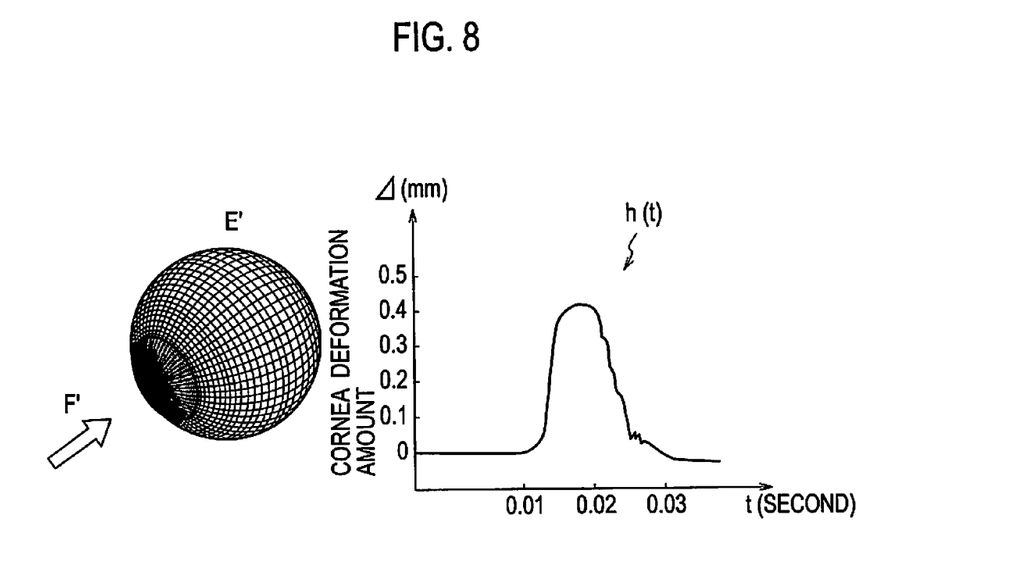
FIG. 8 shows a three-dimensional finite element model of an eyeball, which is used in a non-contact tonometer of the embodiment, and a graph of a time function of a cornea deformation amount obtained by a numerical simulation.

As shown in FIG. 8, a time function h(t) of the numerical simulation is obtained by a numerical simulation which provides virtual air flow spray F' to a precise three dimensional finite element model E' of an eyeball and realizes an extremely close approximation to the actual phenomenon, and the time function h(t) is expressed as a graph similar to the graph of FIG. 5 which is an actual measurement graph.

The time function h(t) of the numerical simulation shown in FIG. 8 can be expressed by the Fourier transform $H(\omega_h)$ as the time function g(t) of the actual cornea deformation amount, as shown in Formula (3) and Formula (4).

[Formula 3]

$$h(t) = \frac{1}{2\pi} \int_{-\infty}^{\infty} H(\omega_h) e^{i\omega_h t} d\omega \qquad (3)$$

[Formula 4]

$$H(\omega_h) = \int_{-\infty}^{\infty} h(t) e^{-i\omega_h t} dt \qquad (4)$$

Figure 9:
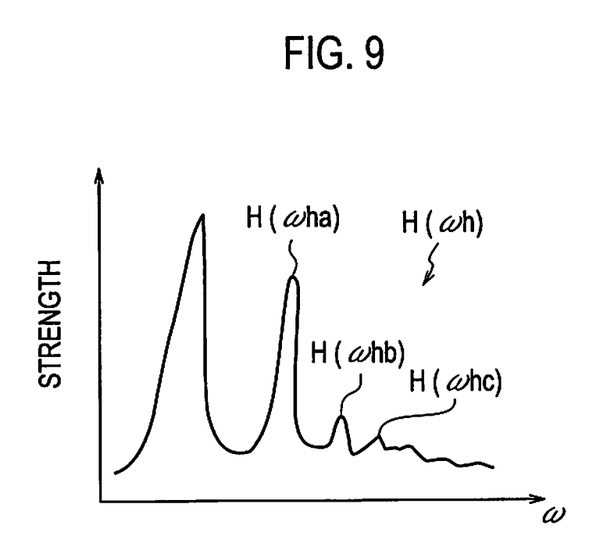
FIG. 9 is a Fourier transform chart of the graph in FIG. 8.

FIG. 9 shows a graph of $H(\omega_h)$ obtained by Fourier-transforming the function h(t) of FIG. 8(b).

Since the eyeball is a nonlinear elastic body, each of the functions g(t) and h(t) can be understood to be a response of a nonlinear system to an input of the air flow spray. Here, when the physical constituent inside an eyeball such as a cornea is changed on the numerical simulation by the finite element method, the content of the nonlinear system changes accordingly and also the function h(t) of the numerical simulation changes. Hence, when $H(\omega_{ha})$ is a component which changes most greatly against the cornea change amount among the components $H(\omega_h)$ constituting the function h(t), $H(\omega_{ha})$ is considered to be a component reflecting the cornea.

The pattern classification program 402 includes a program which accumulates the changes of the function h(t) when the various physical components of the eyeball are changed on the numerical simulation and component data of the Fourier transform $H(\omega_h)$ corresponding to the physical component in a storage device 404 for the pattern classification.

If the pattern classification of the pattern classification program 402 makes a determination such as Formula (5) for the Fourier transform G(ω) which is a component constituting the time function g(t) obtained from an actual measurement for obtaining the cornea deformation amount,

[Formula 5]

$$G(\omega_a) \approx H(\omega_{ha}) \qquad (5)$$

the coefficient of $G(\omega_a)$ is determined to be a numerical value reflecting the cornea, and when the numerical value is denoted by $C_a$, this $C_a$ is treated as a cornea reference.

Figure 10:
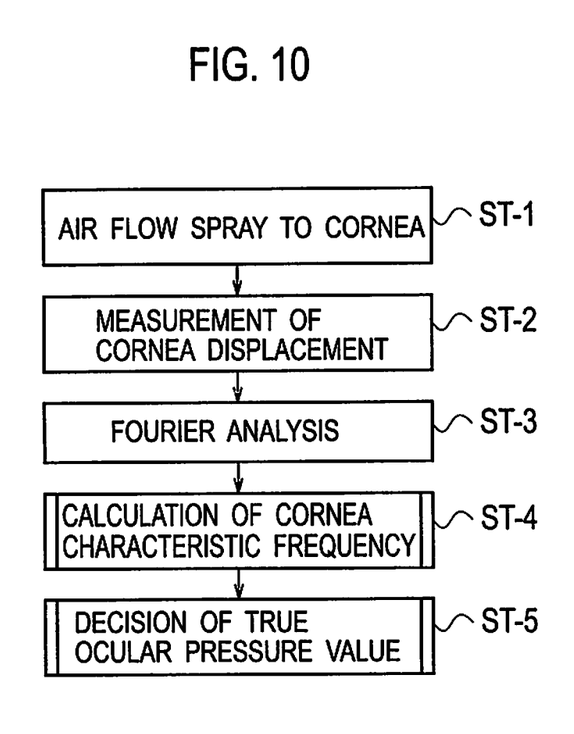
FIG. 10 is a flowchart of true external pressure measurement process in a non-contact tonometer of the embodiment.

FIG. 10 shows the above true ocular pressure measurement procedure in the non-contact tonometer of the present embodiment.

Step ST1: An air flow is sprayed to the cornea C of the eye E to be examined.

Step ST2: A temporal transition of a deformation amount of the cornea C is measured.

Step ST3: Fourier-analysis is carried out to a temporal transition graph of the deformation amount of the cornea C.

Step ST4: A characteristic frequency of the cornea C is calculated.

Step ST5: A true ocular pressure value is obtained based on the characteristic frequency of the cornea C.

Figure 11:
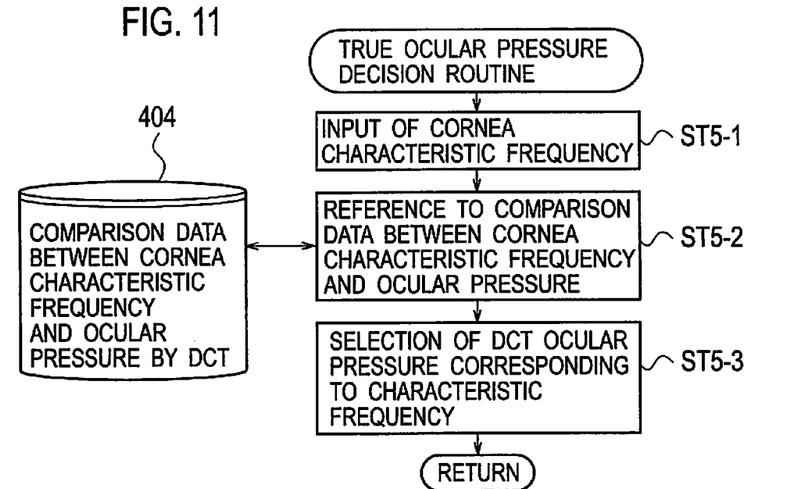
FIG. 11 is a flowchart of the true ocular pressure value decision routine in the flowchart of FIG. 10.

The decision routine of the true ocular pressure value in Step ST5 of FIG. 10 is shown in FIG. 11. Recently, a device which can measure the ocular pressure without being affected by the hardness of the cornea for an ocular pressure measurement value has been considered to be a DCT (Dynamic Contour Tonometer). Hence, the present device preliminarily stores a correspondence between the characteristic frequency of the cornea and an ocular pressure value measured by the DCT in the storage device 404, and calculates a true ocular pressure value from the characteristic frequency of the cornea obtained in the measurement with reference to this comparison data between the characteristic frequency of the cornea and the ocular pressure data by the DCT.

Step S5-1: The measured characteristic frequency of the cornea C is input.

Step S5-2: The comparison data between the cornea characteristic frequency and the ocular pressure which are preliminarily stored in the storage device 404 is referred to.

Step S5-3: A true ocular pressure value corresponding to the cornea characteristic frequency is derived. When an ocular pressure value directly corresponding to the cornea characteristic frequency is not found, the true ocular pressure value is calculated by an interpolation operation or, if necessary, by an extrapolation operation.

The true ocular pressure value corresponding to the characteristic frequency of the cornea C is derived in this manner, and this value is output as a measurement value of the non-contact tonometer in the present embodiment.

Here, when a component $H(\omega_{hb})$ which changes most greatly against a change amount in the stiffness of a sclera, another tissue of the eyeball, among the components $H(\omega_h)$ constituting the above function h(t) is a component reflecting the stiffness of the sclera, and when the pattern classification of the pattern classification program 402 makes a determination such as Formula (6) for the component G(ω) constituting the function g(t) by,

[Formula 6]

$$G(\omega_b) \approx H(\omega_{hb}) \qquad (6)$$

the coefficient of $G(\omega_b)$ is similarly assumed to be a numerical value reflecting the stiffness of the sclera. Then, when the numerical value is denoted by $S_b$, this $S_b$ is output quantitatively as a sclera reference.

Similarly, when a component $H(\omega_{hc})$ which changes most greatly against a change amount in the stiffness of the Zinn's zonule, another tissue of the eyeball, among the components $H(\omega_h)$ constituting the above function h(t) is a component reflecting the stiffness of the Zinn's zonule, the pattern classification of the pattern classification program 402 finds a similar pattern component $G(\omega_c)$ in $G(\omega)$ constituting the function g(t) and the coefficient of this $G(\omega_c)$ is assumed to be a numerical value reflecting the stiffness of the Zinn's zonule. Then, when the numerical value is denoted by $S_c$, this $S_c$ is output quantitatively as a Zinn's zonule reference.

These references are digitized and output from the main control circuit 403.

EXAMPLE 1

Figure 12:
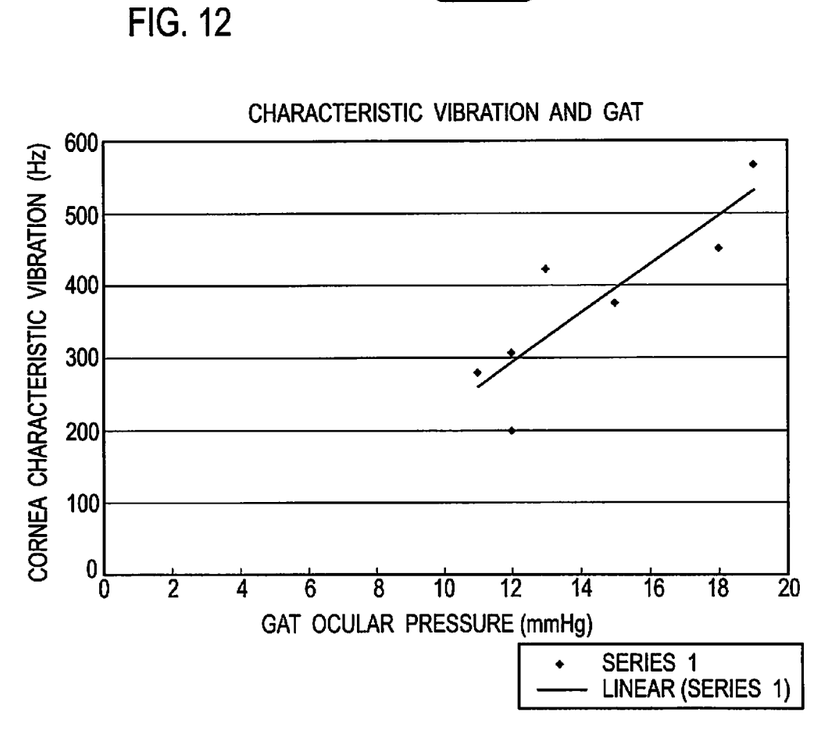
FIG. 12 is a graph of characteristic vibration of a cornea of a normal healthy person's eye and a GAT measurement value.
Figure 13:
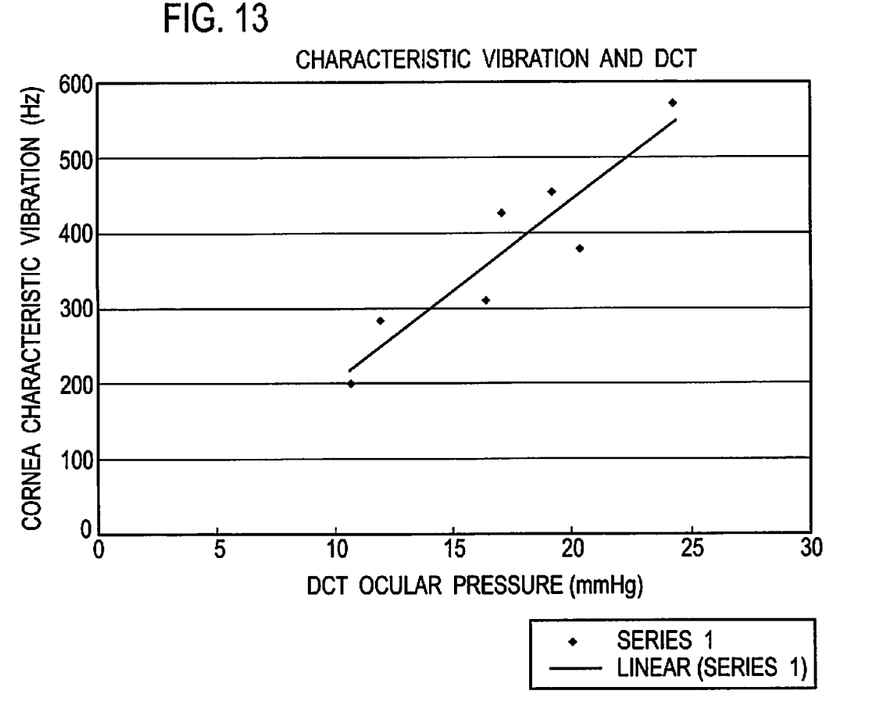
FIG. 13 is a graph of characteristic vibration of a cornea of a normal healthy person's eye and a DCT measurement value.

The graphs shown in FIG. 12 and FIG. 13 are graphs showing correlations of characteristic vibration of the cornea in a normal healthy person's eye obtained by the above measurement system with a Goldmann applanation tonometer (GAT) measurement value and a DCT measurement value, respectively.

FIG. 12 shows that the characteristic vibration of the cornea is significantly correlated with the GAT measurement value, that is, the hardness of the cornea surface.

The DCT is a new type contact tonometer and is said to show a value close to a true ocular pressure among the current ocular pressure measurement methods. FIG. 13 shows that the characteristic vibration of the cornea is significantly correlated with a true ocular pressure.

(Second Embodiment)

Figure 14:
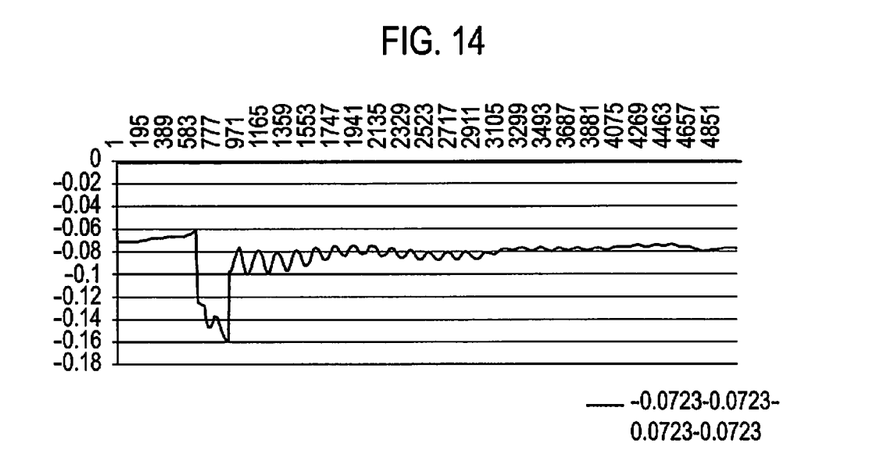
FIG. 14 is a graph of characteristic vibration of a pig's eye and a Tono-Pen measurement value.

The graph shown in FIG. 14 shows a measurement graph of the cornea deformation of a pig eye obtained by the above measurement system using a laser displacement sensor. It is shown that the cornea deformation amount measurement device 300 with a high-speed camera can be displaced by the laser displacement sensor.

By replacing the cornea deformation amount measurement device 300 by the laser displacement sensor, the present invention can perform the measurements of the eyeball physical property measurement system and the ocular pressure measurement system in the same system. Further, while the reference light of the current laser displacement sensor forms a bright point or oval, the reference light may be caused to form a ring shape or a planar shape for the measurement in order to improve the measurement accuracy.

By measuring the cornea deformation amount using the laser displacement sensor instead of measuring the cornea deformation amount with the high-speed camera in this manner, the measurement can be performed with a sufficient accuracy, since the current laser displacement sensor uses a frequency of 5 kHz and has a minimum detection sensitivity of 0.2 μm while the cornea deformation amount measurement by the high-speed camera uses a frequency of 2 kHz and can measure a displacement amount of approximately 300 to 400 μm.

Industrial Applicability

As described above, the present invention can measure a true ocular pressure which eliminates the influence of the stiffness of a cornea. Further, the measurement system of the present invention can quantitatively evaluate a tissue of an eyeball such as a sclera and a Zinn's zonule as well as a cornea. Accordingly, the present invention can be utilized widely for ocular pressure measurement in the ophthalmic treatment.

EXPLANATION OF THE REFERENCE SYMBOLS

C: Cornea
E: Eye to be examined
F: Air flow spray
S: Laser projection light or reflected laser light
L1, L2, L3, and L4: Half mirror
100: Eye front part observation device
110: Eye front part observation system
120: Reference projection optical system
130: Fixation target projection optical system
140: X-Y alignment detection optical system
160: Z alignment reference projection optical system
170: Z alignment detection optical system
180: Ocular pressure measurement system control circuit
200: Air flow spray device
201: Spray amount detection part
202: Pressure sensor
300: Cornea deformation amount measurement device
301: Deformation amount digitization device
400: Analysis device
500: Cornea deformation detection optical system

The invention claimed is:

1. An eyeball tissue characteristic frequency measurement device comprising:
    an air flow spray device for spraying an air flow to a cornea of an eye to be examined and deforming the cornea;
    a cornea deformation amount measurement device for measuring deformation of the cornea caused by the air flow from the air flow spray unit along with elapsed time from the start of the air flow spray;
    a Fourier analysis unit performing Fourier analysis on a relationship between a deformation amount of the cornea obtained by the cornea deformation amount measurement unit and the elapsed time; and
    an eyeball tissue characteristic frequency operation unit obtaining an characteristic frequency of each constituent tissue of an eyeball based on a Fourier analysis result obtained by the Fourier analysis unit
    wherein
    the Fourier analysis unit includes a numerical simulation result preserving unit preserving a numerical simulation result of the eyeball deformation, and a pattern classification unit performing pattern classification for determining to which tissue characteristic frequency of the eyeball a Fourier-analyzed time function corresponds.

2. The eyeball tissue characteristic frequency measurement device according to claim 1, wherein
    the cornea deformation amount measurement device is a high-speed camera.

3. The eyeball tissue characteristic frequency measurement device according to claim 1, wherein
    the cornea deformation amount measurement device is a laser displacement sensor.

4. The eyeball tissue characteristic frequency measurement device according to claim 1, wherein
    the eyeball tissue characteristic frequency operation unit obtains an characteristic frequency of the cornea of the eyeball.

5. A non-contact tonometer utilizing an eyeball tissue characteristic frequency measurement device according to claim 4, the non-contact tonometer comprising:
an ocular pressure operation unit calculating an ocular pressure based on the characteristic frequency of the cornea of the eyeball obtained by the eyeball tissue characteristic frequency operation unit.

* * * * *